(12) United States Patent
Miyazaki et al.

(10) Patent No.: US 10,583,165 B2
(45) Date of Patent: Mar. 10, 2020

(54) METHOD FOR SUPPRESSING INCREASE IN HEART RATE DURING EXERCISE, AND COMPOSITION FOR SUPPRESSING INCREASE IN HEART RATE

(71) Applicant: ASAHI CALPIS WELLNESS CO., LTD., Tokyo (JP)

(72) Inventors: Hidetoshi Miyazaki, Moriya (JP); Kohji Ohki, Moriya (JP)

(73) Assignee: ASAHI CALPIS WELLNESS CO., LTD., Tokyo (JP)

( * ) Notice: Subject to any disclaimer, the term of this patent is extended or adjusted under 35 U.S.C. 154(b) by 0 days.

(21) Appl. No.: 15/573,226

(22) PCT Filed: May 13, 2016

(86) PCT No.: PCT/JP2016/064257
§ 371 (c)(1),
(2) Date: Nov. 10, 2017

(87) PCT Pub. No.: WO2016/182053
PCT Pub. Date: Nov. 17, 2016

(65) Prior Publication Data
US 2018/0085419 A1    Mar. 29, 2018

(30) Foreign Application Priority Data

May 13, 2015   (JP) .................................. 2015-098204

(51) Int. Cl.
| | | |
|---|---|---|
| A61K 38/00 | (2006.01) | |
| A61K 38/01 | (2006.01) | |
| A23L 33/17 | (2016.01) | |
| A61P 9/00 | (2006.01) | |
| A61K 9/00 | (2006.01) | |

(52) U.S. Cl.
CPC ............ A61K 38/018 (2013.01); A23L 33/17 (2016.08); A61K 9/0053 (2013.01); A61P 9/00 (2018.01)

(58) Field of Classification Search
None
See application file for complete search history.

(56) References Cited

U.S. PATENT DOCUMENTS

| | | | | |
|---|---|---|---|---|
| 8,367,614 B2 * | 2/2013 | Hatori | .................. | A61K 31/198 514/16.6 |
| 2012/0015882 A1 * | 1/2012 | Uchida | .................. | A61K 38/05 514/17.5 |

FOREIGN PATENT DOCUMENTS

| | | |
|---|---|---|
| JP | 2-167052 A | 6/1990 |
| JP | 2007-204406 A | 8/2007 |
| JP | 2008-511593 A | 4/2008 |
| JP | 2010-059097 A | 3/2010 |
| WO | 2006/024673 A1 | 3/2006 |

OTHER PUBLICATIONS

Hirohiko Nakamura et al., "Influences of Casein Hydrolysate Ingestion on Cerebral Activity, Autonomic Nerve Activity, and Anxiety", J. Physiol. Anthropol., 2010, pp. 103-108, in particular, pp. 104, 106, 107, vol. 29.
Hidetoshi Miyazaki et al., "Milk casein hydrolysate lowered heart rate during downhill walking exercise and muscle damage after that in middle-aged to elderly men", 12th Asian Congress of Nutrition, May 14, 2015, p. 180, PS-01-a-081.
E. Ya. Stan et al., "On heterogeneity and physiological activity of bovine kappa-casein proteolysis products", Voprosy Pitaniya, 1988, pp. 39-43, vol. 1.
E. Ya. Stan et al., "Isolation amino acid composition and biological effect of peptide bioregulator from bovine kappa casein", Byulleten' Eksperimental' not Biologii i Meditsiny, 1986, pp. 652-655, vol. 102, No. 12.
International Search Report for PCT/JP2016/064257 dated Aug. 9, 2016.

* cited by examiner

Primary Examiner — Jeanette M Lieb
(74) Attorney, Agent, or Firm — Sughrue Mion, PLLC

(57) ABSTRACT

There is provided a method comprising orally administering a composition before and/or during exercise. The composition contains a casein hydrolysate containing a free amino acid and a peptide, or a mixture of the free amino acid and the peptide. The casein hydrolysate is produced by hydrolyzing an animal milk casein, and has an average chain length of 2.1 or less in terms of the number of amino acid residues. There is further provided an oral composition for use in the method. The oral composition contains, as an active ingredient, a casein hydrolysate containing a free amino acid and a peptide, or a mixture of the free amino acid and the peptide. The casein hydrolysate is produced by hydrolyzing an animal milk casein, and has an average chain length of 2.1 or less in terms of the number of amino acid residues. There is still further provided the use of the oral composition for inhibiting increase in heart rate during exercise.

8 Claims, 1 Drawing Sheet

METHOD FOR SUPPRESSING INCREASE IN HEART RATE DURING EXERCISE, AND COMPOSITION FOR SUPPRESSING INCREASE IN HEART RATE

CROSS REFERENCE TO RELATED APPLICATIONS

This application is a National Stage of International Application No. PCT/JP2016/064257 filed May 13, 2016, claiming priority based on Japanese Patent Application No. 2015-098204 filed May 13, 2015, the contents of all of which are incorporated herein by reference in their entirety.

FIELD OF ART

The present invention relates to a method for inhibiting increase in heart rate associated with an exercise load during exercise such as walking, jogging, running, marathon, swimming, bicycle riding, aerobics, tennis, soccer, skiing, or skating. The present invention further relates to a composition for use in the method for inhibiting the increase in heart rate.

BACKGROUND ART

Nowadays more people are in the habit of exercise such as walking or jogging for the purpose of enhancing health or of preventing or improving lifestyle-related diseases. In addition, there are so many potential exercisers (future exercisers), who want to make an exercise habit or think that they should make an exercise habit although they do not have the exercise habit now. However, there are also many people who abandon the making of the exercise habit due to a physical load (i.e. smothering feeling) associated with activation of circulatory system under an exercise load or due to accumulated fatigue.

So-called athletes contend ordinarily with development and improvement of an efficient, effective training method. However, some athletes are obsessed with improvement of athletic performance, and thereby cause overtraining or continue training while enduring accumulated fatigue. This may cause a serious problem of injury.

In this description, hereinafter, those who perform the exercise for the above purpose or as a hobby are referred to as common exercisers, and the athletes are referred to as athletic exercisers.

Some potential common exercisers are considered to abandon the exercise habit because of smothering feeling associated with increase in heart rate during the exercise, which is caused by long-term sedentary lifestyle. In particular, middle-aged and older people, who have been away from the exercise habit for a long period, cause a large increase in heart rate even under a low exercise load, and therefore may avoid the exercise more strongly.

Some athletic exercisers may routinely perform an exercise with an excessive intensity disproportionate to their circulatory functions, out of a sense of obligation to follow a practice schedule, to cause the overtraining or the like. The exercise intensity, which will be described in detail hereinafter, is affected by heart rate during the exercise. The exercise intensity may be relatively lowered by inhibiting the heart rate increase in the same practice.

However, no method for inhibiting the heart rate increase during the exercise based on the above viewpoints has been reported.

Patent Document 1 discloses a lactic acid bacteria-fermented food material having a property of reducing heart rate in a mammal, and use of a composition containing the fermented food material. However, the fermented food material of Patent Document 1 is for reducing "the resting heart rate" of a mammal suffering from a disease such as angina pectoris, hypertension, or atherosclerosis, thereby treating the disease.

Patent Document 2 discloses a heart rate alteration regulator for improving mental or emotional health, and a heart rate alteration regulating method using the regulator. The heart rate alteration regulator contains a hesperidin component, which is a flavonoid derived from a citrus. However, also the invention of Patent Document 2 relates to control of the resting heart rate.

RELATED ART DOCUMENTS

Patent Document 1: JP 2008-511593 W
Patent Document 2: JP 2010-59097 A

SUMMARY OF THE INVENTION

Problem to be Solved by the Invention

As described above, technologies of reducing the resting heart rate or regulating the resting heart rate alteration for treating the disease or improving the mental or emotional health have been reported. However, methods for inhibiting the heart rate increase during the exercise in the common exerciser, the potential common exerciser, and the athletic exerciser have not been known, and compositions for use in the methods have not been known.

Accordingly, an object of the present invention is to provide a method for inhibiting increase in heart rate during exercise, in view of helping a common exerciser or a potential common exerciser to make an exercise habit or to enjoy an exercise more, and in view of reducing a physical load on an athletic exerciser to prevent an injury.

Another object of the present invention is to provide a composition for oral administration in the above method for inhibiting increase in heart rate during exercise, in view of helping a common exerciser or a potential common exerciser to make an exercise habit or to enjoy an exercise more, and in view of reducing a physical load on an athletic exerciser to prevent an injury.

A further object of the present invention is to provide use of the above composition for inhibiting increase in heart rate during exercise, in view of helping a common exerciser or a potential common exerciser to make an exercise habit or to enjoy an exercise more, or in view of reducing a physical load on an athletic exerciser to prevent an injury.

Means for Solving the Problem

As a result of intense research in view of the above objects, the inventors have developed a method for inhibiting increase in heart rate during exercise, which contains administering a particular casein hydrolysate or a component contained therein to a subject (an exerciser) before, during, or both before and during the exercise. The present invention has been accomplished based on this development.

Thus, according to the present invention, there is provided a method for inhibiting increase in heart rate during exercise, comprising orally administering a composition before, during, or both before and during the exercise. The composition contains a casein hydrolysate or a mixture. The casein hydrolysate is produced by hydrolyzing an animal milk casein, contains a free amino acid and a peptide, and has an average chain length of 2.1 or less in terms of the number of amino acid residues, and the mixture contains the free amino acid and the peptide contained in the casein hydrolysate.

It is preferred that the casein hydrolysate is a decomposition product obtained by enzymatically decomposing the animal milk casein with an enzyme derived from a koji mold.

According to the present invention, there is further provided a composition for oral administration in the above method for inhibiting increase in heart rate during exercise. The composition contains a casein hydrolysate or a mixture as an active ingredient. The casein hydrolysate is produced by hydrolyzing an animal milk casein, contains a free amino acid and a peptide, and has an average chain length of 2.1 or less in terms of the number of amino acid residues, and the mixture contains the free amino acid and the peptide contained in the casein hydrolysate.

It is preferred that the composition for inhibiting the heart rate increase contains particular amounts of biopersistent peptides of a dipeptide having an Xaa-Pro sequence and a tripeptide having an Xaa-Pro-Pro sequence.

According to the present invention, there is further provided use of a composition for oral administration for inhibiting increase in heart rate during exercise. The composition contains a casein hydrolysate or a mixture as an active ingredient. The casein hydrolysate is produced by hydrolyzing an animal milk casein, contains a free amino acid and a peptide, and has an average chain length of 2.1 or less in terms of the number of amino acid residues, and the mixture contains the free amino acid and the peptide contained in the casein hydrolysate.

Effect of the Invention

The method of the present invention contains the administration of the particular casein hydrolysate or the components thereof, and thereby is capable of inhibiting the heart rate increase during the exercise. Therefore, the method can help a common exerciser or a potential common exerciser to make an exercise habit or to enjoy the exercise more. Furthermore, the method can reduce a physical load on an athletic exerciser in a training or competition, and prevent an injury.

EMBODIMENTS OF THE INVENTION

Figure 1:
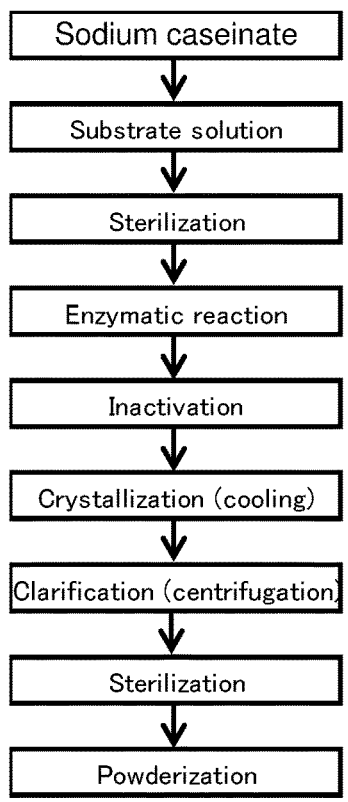
FIG. 1 is an overview process flow diagram of production of a casein hydrolysate according to a working example.

The present invention will be described in more detail below.

The method of the present invention for inhibiting increase in heart rate during exercise contains orally administering a composition before, during, or both before and during the exercise. The composition contains a casein hydrolysate or a mixture. The casein hydrolysate is produced by hydrolyzing an animal milk casein, contains one or more free amino acids and one or more peptides, and has an average chain length of 2.1 or less in terms of the number of amino acid residues, and the mixture contains the free amino acids and the peptides contained in the casein hydrolysate. The composition of the present invention for inhibiting increase in heart rate contains the casein hydrolysate containing the free amino acids and the peptides, or contains the mixture of the free amino acids and the peptides contained in the casein hydrolysate.

The casein hydrolysate used in the present invention is prepared by hydrolyzing the animal milk casein in such a manner that the resultant casein hydrolysate has an average chain length within the particular range in terms of the number of the amino acid residues. The casein hydrolysate contains the mixture of the free amino acids and the peptides, and the weight ratio of the mixture to the total of the casein hydrolysate is preferably 80% by weight or more, more preferably 80% to 90% by weight. It is particularly preferred that the casein hydrolysate contains, as the above described peptides, particular amounts of biopersistent peptides of a dipeptide having an Xaa-Pro sequence and a tripeptide having an Xaa-Pro-Pro sequence. It should be noted that the peptide may be in the form of a peptide salt.

The average chain length may be expressed as the ratio between "the total mole number of all amino acids in a casein acid-hydrolysate" and "the total mole number of the free amino acids and the peptides generated by the above hydrolysis of the animal milk casein of the same weight". The term "casein acid-hydrolysate" means a hydrolysate obtained by hydrolyzing the casein protein completely into the amino acids.

The average chain length may be determined by evaluating the molar concentration of all amino acids and peptides in each of the casein acid-hydrolysate and the casein hydrolysate for the method of the present invention, e.g. in an OPA method using an OPA (o-phthalaldehyde) reagent capable of reacting with an amino group to produce a color, and by performing a calculation using the following equation: Average chain length=(Mole number of the amino acids and peptides in the casein acid-hydrolysate)/(Mole number of the amino acids and peptides in the casein hydrolysate for the method of the present invention).

The biopersistent peptides mean peptides, which exhibit a high decomposition resistance against in vivo peptidases when absorbed intestinally, and include the Xaa-Pro dipeptides and Xaa-Pro-Pro tripeptides having Pro at the carboxyl terminal.

In the present invention, the casein hydrolysate, which is produced by hydrolyzing the animal milk casein, has an average chain length of 2.1 or less in terms of the number of the amino acid residues. The average chain length is preferably 1.1 to 2.1, particularly preferably 1.3 to 2.1. When the average chain length is more than 2.1, the contents of the desired dipeptide, tripeptide, and free amino acid may be lowered, and thus the contents of the desired bioabsorbable and biopersistent peptides may be lowered, thereby failing to achieve the desired advantageous effect.

The weight ratio of the dipeptides having the Xaa-Pro sequence to the total of the free amino acids and the peptides in the casein hydrolysate is usually 5% by weight or more, preferably 5% to 25% by weight. When the ratio is less than 5% by weight, the function of the casein hydrolysate may be deteriorated.

The weight ratio of the tripeptides having the Xaa-Pro-Pro sequence to the total of the free amino acids and the peptides in the casein hydrolysate is usually 1% by weight or more, preferably 1% to 5% by weight. When the ratio is less than 1% by weight, the function of the casein hydrolysate may be deteriorated.

In the casein hydrolysate, the Xaa in the dipeptide having the Xaa-Pro sequence and the tripeptide having the Xaa-Pro-Pro sequence may be any amino acid. Examples of the dipeptides having the Xaa-Pro sequence include Ile-Pro, Glu-Pro, Arg-Pro, Gln-Pro, Met-Pro, and Tyr-Pro, and examples of the tripeptides having the Xaa-Pro-Pro sequence include Ser-Pro-Pro, Val-Pro-Pro, Ile-Pro-Pro, and Phe-Pro-Pro. It is preferred that the casein hydrolysate contains at least one or all of these example dipeptides and tripeptides.

The casein hydrolysate contains the free amino acids in addition to the peptides. The weight ratio of the free amino acids to the total of the free amino acids and the peptides in the casein hydrolysate is usually 35% to 50% by weight, preferably 40% to 45% by weight.

The casein hydrolysate may contain, in addition to the free amino acids and the peptides, about 10% to 20% by weight of a lipid, ash, carbohydrate, dietary fiber, water, or the like, which are usually contained e.g. in a commercially available animal milk casein or the like. One or all of these ingredients may be removed as desired.

For example, the casein hydrolysate may be produced by hydrolyzing the animal milk casein with a group of enzymes capable of decomposing the casein in such a manner that the resultant casein hydrolysate has an average chain length of 2.1 or less in terms of the number of the amino acid residues.

The animal milk casein is a Pro-rich protein with confirmed safety for use in a food or the like. The animal milk casein may be a casein from a cow's milk, horse's milk, goat's milk, sheep's milk, or the like, and is particularly preferably a cow's milk casein.

In the hydrolysis of the animal milk casein, the casein concentration is not particularly limited, and is preferably 3% to 19% by weight to efficiently produce the hydrolysate.

The group of enzymes may be appropriately selected in view of decomposing the casein in such a manner that the casein hydrolysate has an average chain length of 2.1 or less in terms of the number of the amino acid residues. For example, the enzyme group is preferably an enzyme group (X) including a peptidase capable of cleaving a carboxyl-terminus Pro-Xaa bond in Xaa-Pro-Xaa or Xaa-Pro-Pro-Xaa.

The enzyme group (X) preferably includes a serine protease having a serine residue at the active center or a metalloprotease having a metal at the active center. The metalloprotease may be a neutral protease I, a neutral protease II, a leucine aminopeptidase, or the like. It is preferred that the enzyme group (X) includes at least one of these metalloproteases from the viewpoint of obtaining the desired hydrolysate efficiently, in a short time, and in a one-step reaction. The peptidase capable of cleaving the Pro-Xaa sequence is preferably an enzyme having an isoelectric point in the acidic region.

For example, the enzyme group or the enzyme group (X) may be an enzyme group derived from a koji mold such as *Aspergillus oryzae*. Such an enzyme group may be prepared by culturing a fungus in an appropriate medium and by extracting produced enzymes with water. It is particularly preferred that the enzyme group derived from *Aspergillus oryzae* has an isoelectric point in the acidic region.

Examples of the enzyme group derived from *Aspergillus oryzae* include commercial products such as SUMIZYME (trademark) FP, LP, and MP available from Shin Nihon Chemical Co., Ltd., UMAMIZYME (trademark) available from Amano Enzyme Inc., STERNZYME B11024 and PROHIDROXY AMPL (trade names) available from Higuchi Inc., ORIENTASE ONS (trademark) available from Hankyu Bioindustry Co., Ltd., and DENAZYME AP (trademark) available from Nagase Biochemical Ltd. SUMIZYME (trademark) FP available from Shin Nihon Chemical Co., Ltd. is particularly preferred.

The commercially available enzyme groups usually have specific optimum conditions. However, the hydrolysis conditions such as the enzyme amount and the reaction time may be appropriately changed depending on the enzyme group to obtain the desired casein hydrolysate.

For example, the amount of the enzyme group added in the hydrolysis of the animal milk casein may be such that the weight ratio of the enzyme group/the animal milk casein is 1/1000 or more in an aqueous solution. The weight ratio is preferably 1/1000 to 1/10, particularly preferably 1/100 to 1/10, further preferably 1/40 to 1/10.

The reaction conditions may be appropriately selected depending on the enzyme group to obtain the desired casein hydrolysate. For example, the reaction temperature may be 25° C. to 60° C., preferably 45° C. to 55° C., and the pH may be 3 to 10, preferably 5 to 9, particularly preferably 5 to 8. The enzyme reaction time may be 2 to 48 hours, preferably 7 to 15 hours.

The enzyme reaction may be terminated by inactivating the enzymes usually at a temperature of 60° C. to 110° C.

After the termination of the enzyme reaction, the resulting precipitate is preferably removed by centrifugation or filtering if necessary. The amount of the precipitate may be increased by cooling the reaction mixture to a temperature of 5° C. to 10° C. after the termination of the enzyme reaction.

From the resultant hydrolysate, a peptide having a bitter taste or odor may be removed if necessary. Such a bitter-taste or odor ingredient may be removed by using an activated carbon or a hydrophobic resin. For example, the activated carbon may be added to the resultant hydrolysate and interacted with the hydrolysate for 1 to 10 hours, the weight ratio of the activated carbon to the casein used being 1% to 20% by weight. The activated carbon may be removed by a known method such as centrifugation or membrane filtration.

Thus obtained reaction liquid containing the casein hydrolysate may be added directly to a liquid to produce a beverage product such as a soft drink product or a functional drink product. The reaction liquid may be concentrated and dried into a powder to improve the versatility of the casein hydrolysate. The powder can be used as a material for producing various compositions for oral administration.

To the powder may be added various auxiliary additives for improving the nutritional balance or flavor. Examples of such auxiliary additives include various carbohydrates, lipids, vitamins, minerals, sweeteners, flavoring agents, colorants, and texture improvers.

As described above, in the method of the present invention for inhibiting the heart rate increase during the exercise and the composition for use in the method, the active ingredient is the casein hydrolysate having an average chain length of 2.1 or less in terms of the number of the amino acid residues, or the mixture of the free amino acids and peptides contained in the hydrolysate. Furthermore, the weight ratio of the free amino acids and the peptides to the total of the casein hydrolysate is preferably 80% by weight or more.

In the present invention, the amount of the composition administered for inhibiting the heart rate increase during the exercise is preferably such that a dose of the active ingredient is 0.04 to 100 g per a single exercise (one exercise) for a human having a body weight of 50 kg (i.e. 0.8 to 2000 mg/kg body weight). The dose of the active ingredient is preferably 0.2 to 20 g (4 to 400 mg/kg body weight), further preferably 0.3 to 4 g (6 to 80 mg/kg body weight). The administration dose per the unit body weight may be applied to children and adults.

The composition may be administered before, during, or both before and during the exercise. It is preferred that the composition is administered at least before the exercise from the viewpoint of the effects. Furthermore, the composition may be administered continuously after the exercise.

The composition of the present invention for inhibiting the heart rate increase may be in any product form as long as it contains the above-described active ingredient. The composition may be a solid or powder food product, and may be a beverage product. Furthermore, the composition may be in the form of a functional food product, a functional drink product, or a supplement product.

Examples of the food and beverage products include liquid foods, jellies, cookies, biscuits, chocolates, fruit juice beverages, lactic acid bacteria beverages, isotonic beverages, and carbonated beverages. The products may further contain an additive for foods and beverages, such as a sugar, protein, lipid, vitamin, mineral, flavor, or a mixture thereof, as desired.

Examples of dosage forms of the functional food, functional drink, and supplement products include tablets, pills, hard capsules, soft capsules, microcapsules, powders, granules, or liquids.

For example, the composition may be formulated in unit dose form required for generally accepted formulation, using an acceptable carrier, adjuvant, excipient, auxiliary excipient, antiseptic, stabilizer, binder, pH regulator, buffer, thickener, gelatinizer, preservative, lubricant, antioxidant, or the like as required.

Examples of the excipients for the tablets include lactose, sucrose, D-mannitol, D-sorbitol, starches, α-starches, dextrins, crystalline celluloses, low-substituted hydroxypropylcelluloses, sodium carboxymethylcelluloses, gum arabics, pullulans, light anhydrous silicic acids, synthetic aluminum silicates, and magnesium aluminometasilicates. Examples of the lubricants include sugar esters (such as sucrose fatty acid esters and glycerin fatty acid esters), calcium stearate, magnesium stearate, stearic acid, stearyl alcohols, hardened oils (such as vegetable fat powders), waxes (such as white beeswaxes), talcs, silicic acid, and silicon.

The exercise and sport in the present invention will be described below. The exercise and sport in the present invention are not particularly limited, and examples thereof include walking, jogging, running, marathon, swimming, aerobics, boat, baseball, tennis, table tennis, soccer, basketball, volleyball, dance, archery, bicycle riding, bicycle racing, skiing, skating, skateboard, trekking, climbing, diving, and sky-diving. The examples further include motorbike racing and car racing, which may be a high-intensity exercise with a large load on the exerciser, and may cause a heart rate increase to approximately maximum rate at a crucial time.

During the exercise or sport, a common exerciser may suffer from a fatigue feeling or a smothering feeling due to the heart rate increase, and may hate the exercise. On the other hand, an athletic exerciser may conduct an unreasonable training continuously to cause an injury, and may suffer from slowed reflexes or decreased judgment due to accumulated fatigue to cause an injury during the exercise.

The heart rate increase during the exercise can be inhibited to prevent the above problems by carrying out the method of the present invention for inhibiting the heart rate increase during the exercise, i.e. by administering the composition for the method of the present invention before, during, or both before and during the exercise. The method for inhibiting the heart rate increase and the composition for inhibiting the heart rate increase may be referred to simply as the method of the present invention and the composition of the present invention.

In the case of administering before the exercise, the composition is administered preferably at most 3 hours before the start of the exercise, more preferably at most 1 hour before the start, particularly 15 to 45 minutes before the start. The composition is administered before and/or during the exercise, and may be further administered continuously also after the exercise.

The exercise or sport in the present invention may be as described above. The load of the exercise or sport on human body, i.e. the exercise load, may be expressed as the exercise intensity to be described below. In the present invention, the exercise intensity is obtained by the Karvonen method using the following equation (1):

$$\text{Exercise intensity (\%)} = [(\text{Heart rate during exercise} - \text{Resting heart rate}) \div (\text{Maximum heart rate} - \text{Resting heart rate})] \times 100 \qquad (1)$$

In the equation (1), the maximum heart rate is different for different people, and is hard to measure and unpractical. Therefore, the estimate maximum heart rate represented by the following equation (2) is used instead of the maximum heart rate. Thus, in this description, the maximum heart rate in the equation (1) means the estimate maximum heart rate in the equation (2). Incidentally, the maximum heart rate of each person may be precisely measured, and the exercise intensity may be calculated from the measured maximum heart rate.

$$\text{Estimate maximum heart rate} = 220 - \text{age} \qquad (2)$$

According to Satoshi Yamamoto and Hajime Yamazaki, "Recent Concept of Exercise Prescription (Undo Syoho no Saikin no Kangae-kata)", Bulletin (Kiyo) of Sports Medicine Research Center of Keio University, page 33-39, 1999, the exercise intensity of 0% corresponds to the resting state, the exercise intensity of less than 20% corresponds to an extremely-low-intensity exercise, the exercise intensity of 20% to 39% corresponds to a low-intensity exercise, the exercise intensity of 40% to 59% corresponds to a moderate-intensity exercise, the exercise intensity of 60% to 84% corresponds to a high-intensity exercise, the exercise intensity of 85% or more corresponds to an extremely-high-intensity exercise, and the exercise intensity of 100% corresponds to the maximum-intensity exercise. In other words, the exercise intensity of less than 40% corresponds to a low-intensity exercise, the exercise intensity of not less than 40% and less than 80% corresponds to a relatively- or very-high-intensity exercise, and the exercise intensity of 80% or more corresponds to a near-maximum-intensity exercise.

The heart rate may be largely changed in a type of the exercise. The "Heart rate during exercise" in the equation (1) is an average heart rate in a predetermined time during the exercise. Similarly, the "Resting heart rate" in the equation (1) is an average heart rate in a predetermined time in the resting state before the exercise.

The degree of the inhibition of the heart rate increase during the exercise by the method and composition of the present invention depends on the type of the exercise, the amount of the exercise, and the subject person, and therefore cannot be specified definitely. The method of the present invention is capable of reducing the heart rate during the exercise by at least more than 0%, as compared with a case where the method of the present invention is not carried out.

The load of the exercise on the human body is evaluated in terms of the exercise intensity because the load depends on the person. Thus, the load on the human body differs greatly in individuals even under the same exercise amount condition, depending on age, sex, habitually habit, whether they are the common exerciser or the athletic exerciser, etc. For example, even when an exercise is evaluated to be the extremely-low-intensity exercise for an athletic exerciser, the same exercise may be evaluated to be the high- or extremely-high-intensity exercise for an aged person having no exercise habit.

In the case of administering the composition of the present invention in the method of the present invention, the exercise intensity is not particularly limited, and may be any intensity of more than 0%. In view of realizing the heart rate increase inhibition effect, the method of the present invention is carried out preferably during an exercise with an exercise intensity of more than 0% and not more than 60%, more preferably during an exercise with an exercise intensity of 20% to 40%.

The exercise time is not particularly limited as long as the exercise intensity is more than 0%. For example, the exercise time may be several minutes in short-distance sprint such as 50 meter sprint, and may be 5 to 8 hours in ordinary citizen full marathon. The exercise in the method of the present invention may be such a short- or long-distance running. As described above, the method and the composition of the present invention may be used during the exercise with an exercise intensity of more than 0% regardless of the exercise time.

In a case where the exercise time is more than 30 minutes, the composition of the present invention may be administered before the start of the exercise, and may be further administered also during the exercise.

In a case where the composition of the present invention is administered to an athletic exerciser, it is preferred that the method of the present invention and the administration of the composition are performed according to a coaching or instruction of a manager, a coach, an expert trainer, or the like, who can calmly observe and assess the athletic exerciser's condition.

In a case where the composition of the present invention is administered to a common exerciser in a public sports club, a common sports club, a gym, or the like, it is preferred that the administration of the composition is performed according to a coaching or instruction of a coach, a trainer, an instructor, or the like, who can calmly observe and assess the common exerciser's condition.

Alternatively, in a case where the composition of the present invention is provided with an information such as a manual on the administration, the common exerciser and the athletic exerciser may ingest the composition according to their own judgment based on the information. Alternatively, the exercisers may ingest the composition according to their own judgment based on an information from the Internet, such as an e-mail from an owner of the invention or a person with the owner's permission, or a website provided by the owner. In addition, the exercisers may ingest the composition of the present invention and conduct the method of the present invention according to only their own judgment.

EXAMPLES

The present invention will be described below with reference to Examples without intension of restricting the invention.

A production example of a casein hydrolysate for Examples, which is produced by hydrolyzing an animal milk casein, contains a free amino acid and a peptide, and has an average chain length of 2.1 or less in terms of the number of amino acid residues, will be described below. In the following description, unless otherwise noted, the term "casein hydrolysate" means the casein hydrolysate produced in the following production example.

1. Production Example of Casein Hydrolysate

An overview process flow diagram of production of the casein hydrolysate is shown in FIG. 1.

4.5 g of a casein derived from a cow's milk (a casein sodium available from Nippon NZMP Ltd.) was added to 100 g of a distilled water at about 80° C., the resultant was thoroughly stirred, a 1-N sodium hydroxide solution (available from Wako Pure Chemical Industries, Ltd.) was added thereto to adjust the pH to 7.0, and the liquid was cooled to 20° C. to prepare a substrate solution. The substrate solution was heated and sterilized at 95° C. for 10 minutes.

A commercially available enzyme group (SUMIZYME FP (trademark) available from Shin Nihon Chemical Co., Ltd.) was added to the sterilized substrate solution at an enzyme/casein ratio of 1/25 by weight, and the casein was reacted at 50° C. for 11 hours. The enzyme group was that derived from *Aspergillus oryzae*, and contained at least a metalloprotease, a serine protease, a neutral protease I, a neutral protease II, and a leucine aminopeptidase. Then, the solution was heated at 95° C. for 10 minutes, so that the enzyme group was inactivated to obtain a casein hydrolysate solution. The casein hydrolysate solution was cooled to 5° C., and the supernatant liquid was isolated from the precipitate by centrifugation at 3000 rpm for 20 minutes. The supernatant liquid was heated and sterilized at 95° C. for 10 minutes, and dried by spray drying or freeze drying to obtain a powder of the casein hydrolysate.

Ingredients in the obtained casein hydrolysate were analyzed. The protein amount was measured by the Kjeldahl method, and the amino acid content was measured by an amino acid analyzer. The peptide content was calculated by subtracting the amino acid content from the protein amount. Furthermore, the lipid content was measured by an acid hydrolysis method, the ash content was measured by a direct asking method, and the moisture content was measured by an ordinary-pressure heat drying method. The carbohydrate content was calculated by subtracting the contents of these ingredients from 100%. As a result, the amino acid content was 38.5% by weight, the peptide content was 43.8% by weight, the moisture content was 5.8% by weight, the lipid content was less than 0.1% by weight, the ash content was 4.1% by weight, and the carbohydrate content was 7.8% by weight.

2. Average Chain Length of Free Amino Acid and Peptide in Casein Hydrolysate

The average chain length of the free amino acids and the peptides in the casein hydrolysate obtained in the above production example of 1 was determined as follows. The mole number of the casein hydrolysate was measured using an OPA reagent, which was capable of reacting with the amino groups of the free amino acids and the peptides. The mole number of a casein acid-hydrolysate was measured in the same manner. The ratio between measured mole numbers was evaluated.

40 mg of o-phthalaldehyde (a fluorescence analysis reagent, special grade, available from Nacalai Tesque, Inc.) was dissolved in 1 ml of methanol, and 100 μL of β-mercaptoethanol was added thereto. The resultant solution was diluted to 25 mL with a solution containing 25 mL of a 100-mM sodium tetraborate solution and 2.5 mL of a 20% sodium dodecyl sulfate, and was further diluted to 50 mL with a distilled water, to prepare the OPA reagent.

The casein hydrolysate powder obtained in the above production example of 1 was dissolved in an appropriate solvent at an appropriate concentration, and centrifuged at 15000 rpm for 10 minutes. 50 μL of the supernatant was isolated, and 1 mL of the above OPA reagent was added thereto. The resultant was thoroughly stirred, and left at the room temperature for 5 minutes. Then, the absorbance at 340 nm was measured using an absorptiometer (trade name Ubest-35, available from JASCO Corporation).

A 1% casein acid-hydrolysate was prepared, appropriately diluted, and subjected to the same measurement. The relationship between the absorbance and the molar concentration was determined from the measurement results, to obtain a calibration curve. The average chain length was 2.1, which was calculated using the following equation:

Average chain length=(Molar concentration of 1% casein acid-hydrolysate)/(Molar concentration of 1% casein hydrolysate)

3. Measurement of Contents of Peptides in Casein Hydrolysate

The contents of the dipeptides and tripeptides in the casein hydrolysate obtained in the above production example of 1 were measured by an ordinary method using various synthetic standard peptides. The results are shown in Table 1. The weight (mg) of each peptide in 1 g of the casein hydrolysate is shown in Table 1.

TABLE 1

| | Peptide sequence | Content (mg/g)*[1] |
|---|---|---|
| Dipeptide | Ile-Pro | 3.1 |
| | Glu-Pro | 5.9 |
| | Arg-Pro | 5.7 |
| | Gln-Pro | 10.7 |
| | Met-Pro | 5.1 |
| | Tyr-Pro | 13.4 |
| | Other Xaa-Pro | 39.7 |
| | Total of Xaa-Pro | 83.7 |
| Tripeptide | Ser-Pro-Pro | 0.5 |
| | Val-Pro-Pro | 3.4 |
| | Ile-Pro-Pro | 5.0 |
| | Phe-Pro-Pro | 4.0 |
| | Other Xaa-Pro-Pro | 3.2 |
| | Total of Xaa-Pro-Pro | 16.1 |
| | Total | 99.8 |

*[1]Content of a peptide in 1 g of casein hydrolysate

As described above, in the casein hydrolysate, the amino acid content was 38.5% by weight, and the peptide content was 43.8% by weight. Therefore, in the casein hydrolysate, the weight ratio of the dipeptides having the Xaa-Pro sequence to the total of the free amino acids and the peptides was 10.2% by weight. Furthermore, in the casein hydrolysate, the weight ratio of the tripeptides having the Xaa-Pro-Pro sequence to the total of the free amino acids and the peptides was 2.0% by weight.

Example 1

An exercise test using a double-blind placebo-controlled crossover study was carried out under the following conditions to evaluate an effect of inhibiting heart rate increase during exercise.

[1] Subject

Fourteen healthy (normal) males having no exercise habit (40 to 74 years old, with an average age of 53.1 years)

[2] Type and Amount of Exercise

Walking exercise on a downward slope (−5°) at 5 km/h for 30 minutes using a treadmill

[3] Composition for Inhibiting Heart Rate Increase

The casein hydrolysate powder produced by the method of "1. Production example of casein hydrolysate" was tableted with an excipient and a lubricant, to prepare tablets. One tablet had a weight of 0.35 g, and the content of the casein hydrolysate in the tablet was 25% to 30% by weight.

[4] Test Method 1) 30 minutes before the beginning of the exercise, four tablets (1.4 g) were administered to each subject, and the heart rate measurement using electrocardiogram was started. After the administration, the subject was maintained in a resting state until the beginning of the exercise.

2) 30 minutes after the administration, the exercise of [2] was started. The heart rate measurement using electrocardiogram was continued during the exercise.

3) After the exercise, the subject was maintained in a resting state for 30 minutes, and the measurement was terminated.

4) The exercise intensity of each subject was calculated from the heart rate measurement results using the above equations (1) and (2).

The resting heart rates before the exercise, the heart rates during the exercise, and the exercise intensities of the fourteen subjects are summarized in Table 2. In the row of "Average resting heart rate" of Table 2, the average of the resting heart rates of the fourteen subjects measured for 30 minutes is shown, and the standard deviation of the average resting heart rates of the fourteen subjects is shown.

In the row of "Average heart rate during exercise" of Table 2, the average of the heart rates during exercise of the fourteen subjects measured for 30 minutes is shown, and the standard deviation of the average heart rates during exercise of the fourteen subjects is shown.

In the row of "Exercise intensity" of Table 2, the average of the exercise intensities of the fourteen subjects calculated from the average resting heart rates and the average heart rates during exercise is shown, and the standard deviation of the exercise intensities of the fourteen subjects is shown.

Figure 2:
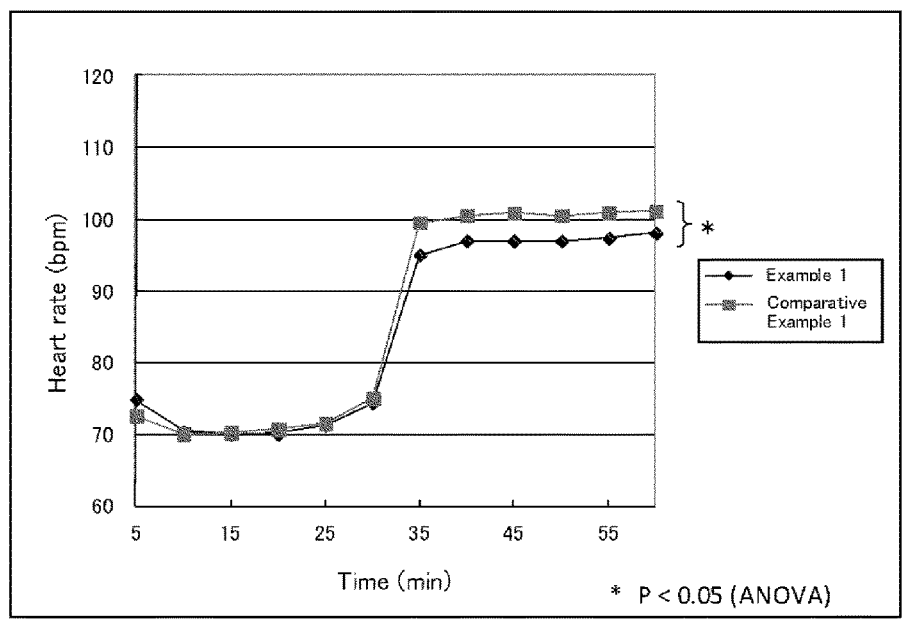
FIG. 2 is a graph showing heart rate changes in exercise tests in Example 1 and Comparative Example 1.

In addition, the heart rate changes in the test are shown in FIG. 2. The heart rates shown in FIG. 2 are average values among the fourteen subjects at each time measured every 5 minutes. The exercise of [2] is started at the time of 30 minutes shown in FIG. 2.

Comparative Example 1

Tablets of Comparative Example 1 were prepared and tested using the same fourteen subjects in the same manner as Example 1 except for using 25% to 30% by weight of a casein sodium as a placebo instead of the casein hydrolysate powder. Incidentally, the test in Comparative Example 1 was carried out on a different day from the test day in Example 1.

The results are shown in Table 2 and FIG. 2. The average values and standard deviations of Comparative Example 1 shown in Table 2 are obtained in the same manner as Example 1. The heart rates of Comparative Example 1 shown in FIG. 2 are average values among the fourteen subjects at each time measured every 5 minutes in the same manner as Example 1.

TABLE 2

|  | Example 1 | | Comparative Example 1 | |
| --- | --- | --- | --- | --- |
|  | Average | Standard deviation | Average | Standard deviation |
| Average resting heart rate (beats/minute) | 71.8 | 13.5 | 71.7 | 17.3 |
| Average heart rate during exercise (beats/minute) | 96.9 | 7.9 | 100.6 | 10.9 |
| Exercise intensity (%) | 26.2 | 14.5 | 30.4 | 17.4 |

As shown in Table 2 and FIG. 2, the heart rate during exercise of Example 1 was about 3.7 beats/minute smaller than that of Comparative Example 1 over the exercise time statistically significantly ($P<0.05$). Thus, the inhibition of the heart rate increase during the exercise was shown in Example 1 statistically significantly ($P<0.05$). Furthermore, as shown in Table 2, the exercise intensity of Example 1 was about 4.2% lower than that of Comparative Example 1 at the same exercise amount due to the effect of inhibiting the heart rate increase. Thus, the tablet of Example 1 exhibited an exercise intensity decrease rate of about 13.8%. Consequently, the composition of the present invention can reduce a load on human body.

Meanwhile, the average resting heart rate of Example 1, measured for 30 minutes after the tablet administration until the beginning of the exercise, was similar to that of Comparative Example 1. Thus, it is clear that the effect of the present application is substantially different from resting heart rate improvement effects.

What is claimed is:

1. A method for inhibiting increase in heart rate of a subject during exercise, comprising orally administering a composition before, during, or both before and during the exercise to the subject, wherein the composition contains a casein hydrolysate or a mixture, the casein hydrolysate is produced by hydrolyzing an animal milk casein, contains a free amino acid and a peptide, and has an average chain length of 2.1 or less in terms of the number of amino acid residues, and the mixture contains the free amino acid and the peptide contained in the casein hydrolysate.

2. The method according to claim 1, wherein the casein hydrolysate is produced by enzymatically decomposing the animal milk casein with an enzyme derived from a koji mold.

3. The method according to claim 1, wherein a dose of the casein hydrolysate or the mixture in the oral administration is 0.8 to 2000 mg/kg body weight.

4. The method according to claim 1, comprising orally administering the composition one or more times per the exercise.

5. The method according to claim 2, wherein a dose of the casein hydrolysate or the mixture in the oral administration is 0.8 to 2000 mg/kg body weight.

6. The method according to claim 2, comprising orally administering the composition one or more times per the exercise.

7. The method according to claim 3, comprising orally administering the composition one or more times per the exercise.

8. The method according to claim 5, comprising orally administering the composition one or more times per the exercise.

* * * * *